United States Patent [19]

Mattingly et al.

[11] Patent Number: 5,669,819
[45] Date of Patent: Sep. 23, 1997

[54] CHEMILUMINESCENT PHENANTHRIDINIUM

[75] Inventors: Phillip Gregory Mattingly; Larry Gene Bennett, both of Grayslake, Ill.

[73] Assignee: Abbott Laboratories, Abbott Park, Ill.

[21] Appl. No.: 442,052

[22] Filed: May 16, 1995

Related U.S. Application Data

[62] Division of Ser. No. 368,258, Jan. 3, 1995, Pat. No. 5,468,646, which is a continuation of Ser. No. 371,763, Jun. 23, 1989, abandoned, which is a continuation of Ser. No. 921,979, Oct. 22, 1986, abandoned.

[51] Int. Cl.$^6$ .................................................. G01N 31/00
[52] U.S. Cl. .................. 436/501; 435/6; 435/7.1; 435/968; 436/518; 436/536; 436/544; 436/546; 436/548; 436/800; 530/389.8; 536/27.1; 546/104
[58] Field of Search .................... 435/6, 7.1, 968; 436/501, 518, 536, 544, 546, 548, 800, 805; 530/389.8; 536/27.1; 546/110, 108, 104

[56] References Cited

U.S. PATENT DOCUMENTS

| | | | |
|---|---|---|---|
| 3,431,264 | 3/1969 | Sheehan et al. | 546/104 |
| 3,539,574 | 11/1970 | Sheehan et al. | 546/104 |
| 4,338,213 | 7/1982 | Tseng et al. | 544/106 |
| 4,687,747 | 8/1987 | Lin | 436/518 |
| 4,745,181 | 5/1988 | Law et al. | 530/387 |
| 5,281,712 | 1/1994 | McCapra et al. | 546/104 |
| 5,284,951 | 2/1994 | McCapra et al. | 546/107 |
| 5,290,936 | 3/1994 | Beheshti et al. | 546/104 |
| 5,308,750 | 5/1994 | Mehta et al. | 435/5 |
| 5,321,136 | 6/1994 | McCapra | 546/104 |
| 5,338,847 | 8/1994 | McCapra | 546/104 |
| 5,395,938 | 3/1995 | Ramakrishman | 546/104 |
| 5,468,646 | 11/1995 | Mattingly et al. | 436/501 |

FOREIGN PATENT DOCUMENTS

| | | |
|---|---|---|
| 082636 | 6/1983 | European Pat. Off. . |
| 0170415 | 2/1986 | European Pat. Off. . |
| 0257541 | 3/1988 | European Pat. Off. . |
| 0257754 | 3/1988 | European Pat. Off. . |
| 0263657 | 4/1988 | European Pat. Off. . |
| 322926A2 | 7/1989 | European Pat. Off. . |
| 3628573 | of 0000 | Germany . |
| 1461877 | 1/1977 | United Kingdom . |

OTHER PUBLICATIONS

F. McCapra, Chapter 9 entitled "*Chemiluminescent Reactions of Acridines*"in Chemistry of Heterocyclic Compounds, vol. 9:615–630 (1973).
R. Hart et al., "The Use of Acridinium Ester Labelled Streptavidin in Immunoassays", *J. Immunol. Methods*, 101:91–96 (1987).
Richardson, "*Clinical Chemistry*", 31(10):1664–1668, (1985).
Weeks et al., *Clin. Chem.*, 29/8: 1474–1479 (1983).
Catherall et al., *J Chem. Soc. Faraday Trans.*, 2,80: 823–834 (1984).
Gill, *Aldrichin ACTA*. 16: 59–61 (1983).
Kobayashi et al., *Anal Chem.*, 52: 424–427, (1980).
Kricka et al., "Diagnostic Medicine". 1:45–52 (1984).
Miyaguchi et al., *J. Chromatogr.*, 303: 173–176 (1984).
Schuster et al., *Advances in Physical Organic Chemistry*, 18: 187–238 (1984).

*Primary Examiner*—Carol A. Spiegel
*Attorney, Agent, or Firm*—Priscilla E. Porembski

[57] ABSTRACT

Acridinium sulfonylamides and isomers, such as phenanthridinium sulfonylamides, may be employed in applications including chemiluminmescent immunoassays. Methods for synthesis of these compounds include contacting an amine with a sulfonylhalide to form a sulfonamide and acylating with an activated carboxylic acid of an acridine or isomer thereof. The N-sulfonyl-9-acridinium carboxamide and isomers may be conjugated to antigens, haptens, antibodies, and nucleic acids for use in chemiluminescent assays.

14 Claims, 1 Drawing Sheet

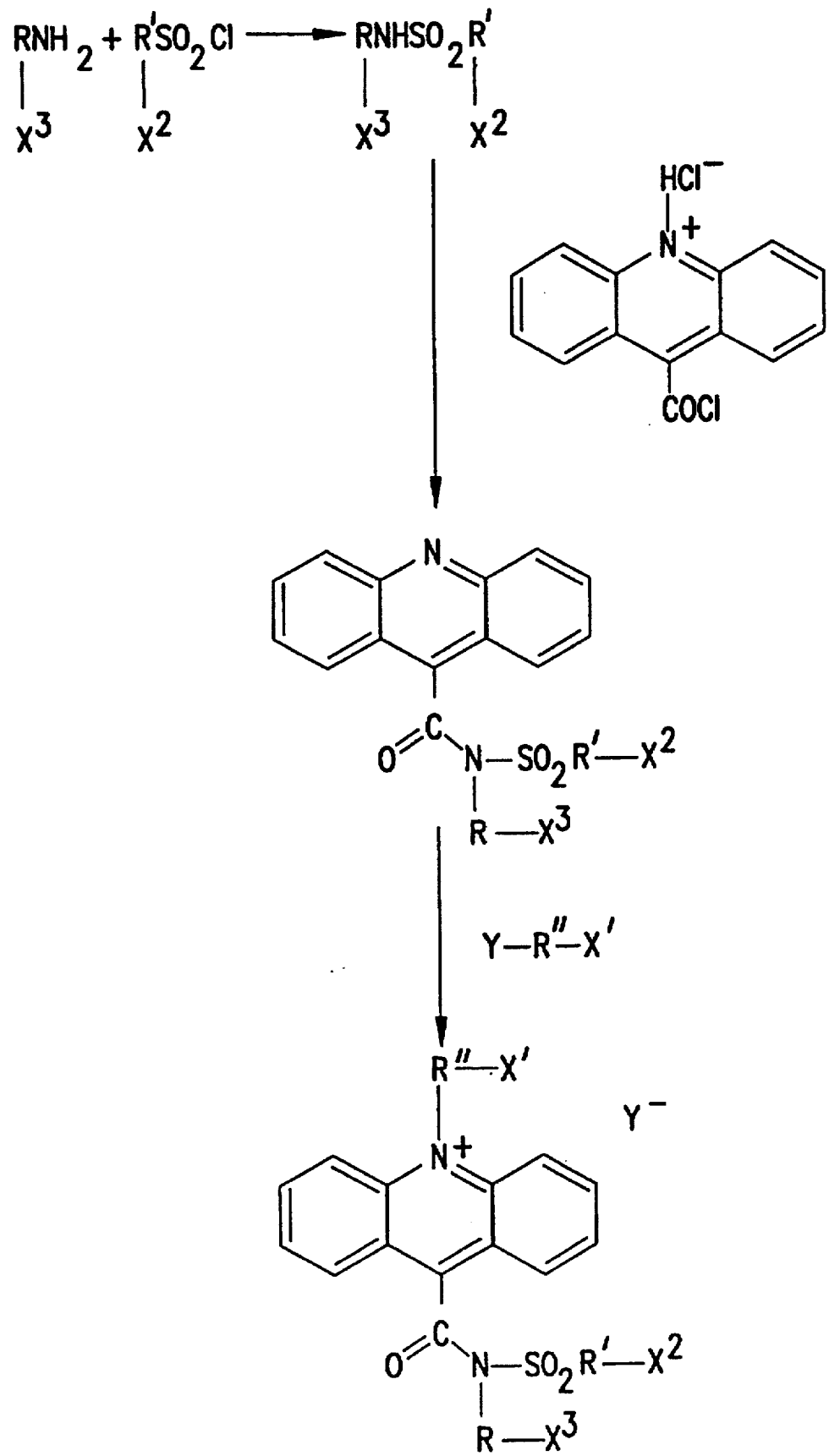

CHEMILUMINESCENT PHENANTHRIDINIUM

This application is a division of U.S. patent application Ser. No. 08/368,258 filed Jan. 3, 1995, now U.S. Pat. No. 5,468,646, which is a continuation of U.S. Ser. No. 07/371,763 filed Jun. 23, 1989, now abandoned, which is a continuation of U.S. Ser. No. 06/921,979, filed Oct. 22, 1986, now abandoned.

BACKGROUND

The present invention relates in general to chemiluminescent methods and materials and in particular to methods and materials involving chemiluminescent acridinium and phenanthridinium salts.

Chemiluminescence may be defined as the generation of light from a chemical reaction. The mechanism of most chemiluminescent reactions is not known in detail, but a generalized mechanism [Schuster et al., *Advances in Physical Organic Chemistry*, 187–238 (1984)] may be outlined:

$$A \rightarrow B^* \rightarrow B + h\nu$$

Compound A undergoes a chemical reaction (usually oxidation) to yield a product in an electronically excited State ("B*"). As it returns to the ground state ("B"), this product gives up energy in the form of light ("hv").

Although competing dark reactions may decrease the efficiency of the overall reaction to less than 1%, some bioluminescent systems may achieve 60–70% efficiency, and, in many cases, limits of detection in the femtomole ($10^{-15}$ mole) to attomole ($10^{-18}$ mole) range have been recorded.

Chemiluminescence has been used for a variety of purposes in analytical chemistry where other methods fail to have adequate sensitivity. In immunodiagnostics, chemiluminescent immunoassays ("CLIA") may thus match or exceed the sensitivity of radioimmunoassays ("RIA") or enzyme immunoassays ("EIA") [Kricka et al., *Diagnostic Medicine*, 1, 45–52 (1984)].

Luminol and isoluminol derivatives are the most widely used chemiluminescent reagents for immunoassays. The light-yielding reaction is initiated by oxidation with alkaline hydrogen peroxide in the presence of catalysts such as microperoxidase or transition metal ions. Light emission occurs at about 465 nm, which corresponds to the fluorescence emission of the product, aminopthalic acid. Aminobutylethyl isoluminol ("ABEI") may be used as a label in immunoassays and is commercially available.

A second group of chemiluminescent reagents, aryl oxalates [Gill, *Aldrichimica Acta*, 16, 59–61 (1983) and Catherall et al., *J. Chem. Soc. Faraday Trans.* 2, 80, 823–834 (1984)], have been used as commercial cold light sources [see e.g., Tseng et al., U.S. Pat. No. 4,338,213] and in high performance liquid chromatography ("HPLC") detectors [Kobayashi et al., *Anal. Chem.*, 52, 424–427 (1980) and Miyaguchi et al., *J. Chromatogr.*, 303, 173–176 (1984)]. It is thought that these derivatives react with hydrogen peroxide in buffered or unbuffered solvents to give a dioxetan-dione which decomposes quickly to give $CO_2$ in an excited state. Energy is then transferred by electron transfer to a fluorescer molecule which emits light.

A third group of reagents, 10-methyl-acridinium-9-carboxylic acid aryl esters, are chemiluminescent in the presence of alkaline hydrogen peroxide and in the absence of a catalyst. The mechanism is thought to involve initial attack by a hydroperoxide anion, followed by intramolecular displacement of the phenolate (the "leaving group") to give a strained dioxetan-one. The strained dioxetan-one decomposes to $CO_2$ and excited N-methyl-acridone, which emits light at 430 nm. Carboxy-substituted acridinium salts have been used as labels in immunoassays [Weeks et al., *Clin. Chem.*, 29, 1474–79 (1983); Campell et al., European Patent Application No. 82,636; and McCapra et al., UK Patent No. GB 1,461,877]. Also, 5-methyl-phenanthridinium-6-carboxylic acid aryl esters, which are isomeric with the acridinium aryl esters, have been used as labels in immunoassays [Lin et al. European Patent Application No. 170,415].

Despite their usefulness in immunoassays, antibody-conjugated phenyl 10-methyl-9-acridiniumcarboxalates, in our hands, are unstable due to hydrolysis above pH 4.0 (–20° C. to 40° C.), losing greater than 10% of their activity within three days. Although acridinium esters are stable below pH 4.0, conjugate antibodies are often not stable in this pH range.

In Tseng et al., supra, bis-N-alkyl-N-trifluoromethyl sulfonyl oxalamides are indicated to be more stable than the corresponding aryl esters and are also indicated to be as efficient. The nucleofugacity of the phenol and the trifluoromethyl sulfonamide are indicated to be comparable, i.e. it is indicated that each has a $pK_a$ of about 7. Gill, supra, "looks forward" to the development of a particular sulfonyl oxalamide as an example of an oxalate with "higher" quantum efficiency.

BRIEF DESCRIPTION OF THE DRAWINGS

The FIGURE illustrates the synthesis of a 10-alkyl-N-sulfonyl-9-acridinium carboxamide according to the present invention.

SUMMARY OF THE INVENTION

The present invention provides chemiluminescent compounds identified by the formula

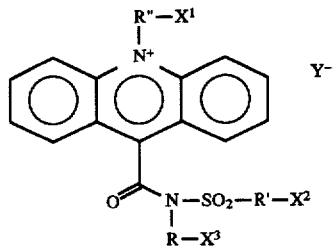

and isomers thereof including isomers identified by the formula

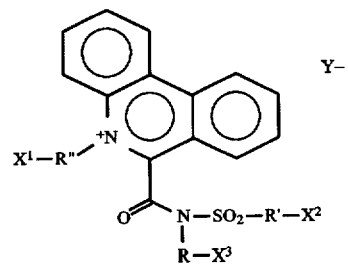

wherein R, R', R", $X^1$, $X^2$, and $X^3$ are substituents which do not interfere with effective chemiluminescence, with the proviso that R—$X^3$, R'—$X^2$ and R"—$X^1$ may be independently hydrogen. More specifically, R, R' and R" may be spacer arms and $X^1$, $X^2$ and $X^3$ may be independently members of the group consisting of hydrogen, carboxy, carboalkoxyl, carboxamido, carboaryloxy, cyano, carboximido, isocyanato, isothiocyanato, sulfo, sulfonyl halide, carbonyl halide, N-succinimidyloxycarbonyl and N-maleimide groups. Y is an appropriate counterion and may be selected from the group consisting of sulfate, alkylsulfate, halosulfate, haloborate, haloacetate, halophosphate, phosphate and halide.

R, R', and R" may independently include a member selected from the group consisting of alkylene, arylene, substituted alkylene and substituted arylene alkenylene groups, such that one or more hydrogens or open valences of said member is replaced by an alkyl, aryl, alkylene, substituted alkyl, substituted alkylene, substituted aryl, alkoxy, aryloxy, halonitro, amino, protected amino, substituted amino, hydroxy, protected hydroxy, oxo, thio, imino, mercapto or substituted mercapto group; or such that one or more carbon atoms of the member is replaced by a heteroatom. The heteroatom may be selected from the group consisting of nitrogen, phosphorus, sulfur and oxygen.

R, R' and R" independently may also be spacer arms of the formula

where n=0–50. Specifically, R" may be —$CH_2$— and $X^1$ may be —H.

The currently most preferred compounds according to the present invention for use in chemiluminescent immunoassays are 10-methyl-N-[2-carboxyethyl]-N-tosyl-9-acridinium carboxamide, 10-(3-sulfopropyl)-N-(2-carboxyethyl)-N-tosyl-9-acridinium carboxamide and 10-(3-sulfopropyl)-N-(3-sulfopropyl)-N-tosyl-9-acridinium carboxamide.

A method, according to the present invention, for preparation of a chemiluminescent compound includes the steps of contacting an amine identified by the formula

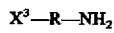

with a sulfonylhalide identified by the formula

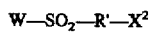

in an inert solvent in the presence of base to form a sulfonamide anion and metal ion identified by the formulas

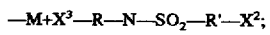

and acylating with an activated 9-acridinecarboxylate compound according to the present invention, wherein W is selected from the group consisting of chloro and fluoro groups, wherein M is selected from the group consisting of Li, Na and K, wherein the activative group is selected from the group consisting of halo, imidazolo, N-hydroxysuccinimidyl and azido groups and wherein all other symbols are as defined above.

A conjugate according to the present invention may be formed by covalently coupling an antibody, a hapten, an antigen or a polynucleotide (e.g., DNA or RNA) to a chemiluminescent compound according to the present invention, and a method for performing a chemiluminescent assay comprises the step of exposing a sample to be tested to the conjugate in order to detect the presence of a substance specifically reactive with the conjugate, e.g., a specific antigen, a specific antibody or a complementary polynucleotide (i.e., a polynucleotide which forms sequence-specific hydrogen bonds with the polynucleotide conjugate according to the present invention).

DETAILED DESCRIPTION

The problem of acridinium aryl ester instability is approached in the present invention by changing the leaving group from a phenolate to a sulfonamide anion. While both leaving groups have a $pK_a$ of about 10, the acridinium sulfonylamide has the additional stabilization associated with amide bonds. This is reflected in a comparison in the infrared of the carbonyl stretching frequency of the aryl ester (1730 $cm^{-1}$) with that of the sulfonylamide (1680 $cm^{-1}$).

A class of acridinium salts, 10-alkyl N-alkyl (aryl) sulfonyl-N-alkyl(aryl) 9-acridinium carboxamide salts, was prepared according to the general scheme illustrated in the FIGURE. In the FIGURE, R, R' and R" are substitutents which may function as spacer arms, solubility modifiers and/or reactivity modifiers but which do not interfere with the chemiluminescent reaction. ("Interfere" is defined herein to mean "prevent the production of effective chemiluminescence", i.e., prevent production of chemiluminescence to the extent that the compound is not useful for the intended application.) Also in the FIGURE, $X^1$, $X^2$, $X^3$ are substituents which may function as solubility enhancers and/or as reactive groups for linkage to an analyte or as groups which may be readily converted to such reactive or linker groups by means well known to those skilled in the art. Y is a counterion in the FIGURE.

Salts produced according to the scheme of the FIGURE have generated light upon oxidation with alkaline hydrogen peroxide. The compounds were made from readily available amines ($X^3$—$RNH_2$) and sulfonyl chlorides ($X^2$—R'$SO_2$Cl). When acylated with 9-chlorocarbonyl acridine, the intermediate sulfonamide ($X^3$—RNH—$SO_2$R'—$X_2$) gave a new class of acridine compounds, which on alkylation gave the acridinium salts. Similarly, substitution of a 6-chlorocarbonyl phenanthridine for the acridine in this scheme gives rise to a new class of phenanthridinium salts. These acridinium and phenanthridinium salts are useful for chemiluminescent labeling of proteins, nucleic acids and small molecules used in diagnostic testing.

Several acridinium sulfonylamides were prepared which have specific activity and stability suitable for use in diagnostic testing, particularly in CLIA. The synthesis of these compounds allows for the introduction of a variety of functional groups ($X^1$, $X^2$, $X^3$) which may be used in antibody labeling. In addition, the kinetics of the chemiluminescent reaction may be controlled by the choice of the substitutents (R, R') on the sulfonamide leaving group.

The compounds were evaluated for their efficiency by diluting 20 µl of a $10^{-9}$M solution of the compound with 300 µl of 0.1N HCL, then adding 150 µl of 0.03% $H_2O_2$ in 0.2N NaOH to trigger the chemiluminescence. Chemiluminescence was measured on a photon-counting luminometer. The light output was recorded as total photon counts, from which the efficiency of each compound was calculated as counts/mole. These are relative numbers, since the efficiency of the photon counting was instrument-dependent. Direct comparisons of compounds were carried out on the same instrument. The results are presented in Table 1 in which the structures may be identified by the formula

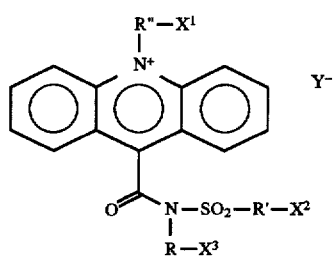

wherein R"—X¹ is $CH_3$, and R'—X² and R—X³ are as indicated in Table 1, chemiluminescent output is abbreviated "CTS/MOLE," the time required for total light output is abbreviated "INT. TIME" and the time required to reach peak light output is abbreviated "PEAK CTS."

TABLE 1

| R'—X² | R—X³ | CTS/MOLE ($\times 10^{-18}$) | INT. TIME | PEAK CTS (SEC) |
|---|---|---|---|---|
| $CF_3$ | $C_6H_5$ | 12 | 1 | 0.22 |
| o-$NO_2C_6H_4$ | $C_6H_5$ | 10 | 2 | 0.23 |
| p-Br—$C_6H_4$ | $C_6H_5$ | 9 | 2 | 0.24 |
| $CF_3$ | i-$C_3H_7$ | 15 | 2 | 0.25 |
| p-$NO_2$—$C_6H_4$ | n-$C_4H_9$ | 8 | 2 | 0.25 |
| o-$NO_2$—$C_6H_4$ | i-$C_3H_7$ | 11 | 2 | 0.25 |
| p-$CH_3C_6H_4$ | $C_6H_5$ | 9 | 2 | 0.27 |
| o-$NO_2C_6H_4$ | n-$C_4H_9$ | 6 | 2 | 0.29 |
| 2,4-di-$NO_2C_6H_3$ | n-$C_4$—$H_9$ | 5 | 2 | 0.32 |
| n-$BrC_6H_4$ | n-$C_4H_9$ | 7 | 3 | 0.44 |
| p-$BrC_6H_4$ | i-$C_3H_7$ | 12 | 6 | 0.44 |
| p-$CH_3C_6H_4$ | n-$C_4H_9$ | 5 | 6 | 0.98 |
| p-$CH_3C_6H_4$ | i-$C_3H_7$ | 8.3 | 10 | 0.96 |
| 2,4,6-$(C_3H_7)_3C_6H_2$ | n-$C_4H_9$ | 14 | 20 | 4.08 |
| 2,4,6-$(CH_3)_3C_6H_2$ | n-$C_4H_9$ | 5 | 50 | 11.6 |
| $CF_3$ | $C_6H_4CHCO_2Bn$ | 4 | 2 | — |

All of the tested compounds were efficient ($5-20\times10^{18}$ counts/mole). The specific activity was insensitive to the nature of the R and R' groups at locations indicated above; however, the time required to reach peak light output and the time required for total light output differed by a factor of 50 between the fastest and slowest compounds. Electron withdrawing groups in R and R' increased the reaction rate while bulky, electron-donating groups decreased the reaction rate. Although chemiluminescent compounds according to the present invention which have a chemiluminescent lifetime of 2–10 seconds are preferred for immunoassays, compounds having shorter lifetime may be useful as a source of intense, pulsed light, and compounds having a longer lifetime may be useful as "cold light" sources.

The stability of compounds prepared according to the present invention was assessed in several ways. First, the compounds were diluted to sub-nanomolar solutions in aqueous buffer at pH 5–7. The solutions were incubated at room temperature and at 45° C., while the decrease in chemiluminescence was monitored over time. This provided qualitative results whereby the relative stability of the compounds was determined. Anomalous results due to non-specific adsorption of the compounds on the incubation container were minimized by the addition of detergents, protein, and the like. Unambiguous, quantitative results were obtained by monitoring millimolar solutions of the compounds by reverse phase high performance liquid chromatography ("HPLC"). The stability of these compounds was affected by R and R' in the same way as were the kinetics of the chemiluminescence reaction, i.e. electron withdrawing groups destabilized and bulky electron donating groups stabilized the compounds.

Although other techniques may be employed to label antibodies, the NHS activation method is presently preferred. Other materials which function well according to the present invention include polyclonal antibodies, monoclonal antibodies, Fab antibody fragments, all of which are hereinafter included in the general term "antibody," haptens, antigens, nucleic acid probes, and non-antibody, binding proteins capable of binding complementary small molecular weight analytes (for example, folate binding protein, which binds folic acid, and intrinsic factor, which binds Vitamin $B_{12}$). Antibody conjugates retain more than 80% chemiluminescence after being heated at 45° C. for four weeks.

A solid phase sandwich immunoassay system for assaying hepatitis B surface antigen ("HBsAg") (Abbott Laboratories, Abbott Park, Ill.) was employed to compare CLIA according to the present invention with RIA. The type of antibody-coated bead, diluent, incubation conditions, washing conditions and antibody preparation were the same except that the antibody was labeled with $^{125}I$ by the chloramine T method for RIA and labeled with NHS-activated N-sulfonyl-9-acridinium carboxamide for CLIA.

A solid phase sandwich immunoassay for human thyroid stimulating hormone (hTSH) was used to compare CLIA with EIA (Abbott Laboratories, Abbott Park, Ill.). The EIA employed a horseradish peroxidase ("HRPO")-labelled antibody while the CLIA used an NHS-activated N-sulfonyl-9-acridinium carboxamide.

The present invention is more specifically described in the following examples. In Example 1, the preparation of sulfonamides which are useful in constructing compounds according to the present invention is set forth. Example 2 includes a description of the preparation of N-sulfonyl-9-acridinecarboxamides according to the present invention. In Example 3, the preparation of 10-methyl N-sulfonyl-acridinium carboxamides is described. Examples 4–6 contain descriptions of syntheses of p-toluenesulfonyl (tosyl) compounds according to the present invention. In Example 7, the preparation of acridinecarboxamides is illustrated.

Example 8–10 contain methods for synthesis of some acridinium carboxamides and products thereof according to the present invention. In Example 11, an evaluation of the chemiluminescence of N-sulfonyl-acridinium carboxamide compounds according to the present invention is provided. Example 12 includes a report of a stability test of an acridinium carboxamide according to the present invention. In Example 13, the temperature and pH stability of two acridinium carboxamides according to the present invention is compared to the temperature and pH stability of an acridiumcarboxylate. Example 14 is a description of a method for conjugating an antibody, specifically an immunoglobulin G ("IgG") antibody, with a compound according to the present invention. The results of a heat stability study of a conjugate according to Example 14 are presented in Example 15. Example 16 includes a description of the preparation of anti-HBsAg acridinium-labeled conjugate as well as a comparison of the sensitivity observed in CLIA and RIA assays employing those conjugates. In Example 18, the synthesis of a phenanthridinium compound according to the present invention is described. Example 17 describes an anti-hTSH acridinium-labeled conjugate along with a comparison to an EIA system.

EXAMPLE 1

General Method for Preparation of Sulfonamides

Amine starting materials for compounds 1–13 and 17–21 are available from Aldrich Chemical Co., Milwaukee, Wis.

For compounds 14–16 and 22–25, the appropriate aminocarboxylic acid (as obtained from Aldrich Chemical Co., Milwaukee, Wis.) was esterified according to standard, published procedures to provide the starting materials.

In order to prepare a sulfonamide according to the present invention, the corresponding amine (200 mole percent) was dissolved in anhydrous methylene chloride, and was treated dropwise at 0° C. with a solution (100 mole percent) of the sulfonyl chloride or anhydride. The solution was poured into anhydrous ether (5 volumes), washed with 1.4M $H_3PO_4$ (25 ml) and then brine (25 ml), and dried over $MgSO_4$. After filtering and evaporating, crude sulfonamides were crystallized from an appropriate solvent.

The following sulfonamides were prepared in this manner. In the description accompanying the name of each compound, the abbreviation "MS" identifies peaks, such as the base peak ("M+") in the mass spectrum at a location (i.e., at an m/e) specified by the symbol "@". A melting point ("$M_p$") or an indication that the material is a liquid at room temperature (e.g. "oil") or decomposes before melting ("decomp.") may be provided. Each compound is identified by a "compound number" (1–25 in this Example) followed by an "identifying number" (e.g. 13513-227) and a chemical name.

1. 13513-227 N-Phenyl-p-toluenesulfonamide. MS $M^+$ @ 247. $M_p$ 100°–102° C.
2. 13513-228 N-Phenyl-p-bromobenzenesulfonamide. MS $M^+$@311. $M_p$ 115°–117° C.
3. 13513-229 N-Phenyl-o-nitrobenzenesulfonamide. MS $M^+$ @ 278. $M_p$ 112°–113° C.
4. 13513-231 N-Phenyl-p-nitrobenzenesulfonamide. MS $M^+$ @ 278. $M_p$ 168°–170° C.
5. 13513-232 N-Phenyl-2,4-dinitrobenzenesulfonamide. MS $M^+$ @ 323. $M_p$ 110°–113° C.
6. 13513-233 N-Phenyl-trifluoromethanesulfonamide. MS $M^+$ @ 225. $M_p$ 65°–67° C.
7. 13514-001 N-Isopropyl-p-toluenesulfonamide. MS $M^+$ @ 213. $M_p$ 50°–51° C.
8. 13514-002 N-Isopropyl-p-bromobenzenesulfonamide. MS $M^+$ @ 277. $M_p$ 95°–96° C.
9. 13514-003 N-Isopropyl-o-nitrobenzenesulfonamide. MS $M^+$ @ 244. $M_p$ 119°–120° C.
10. 13514-004 N-Isopropyl-trifluoromethanesulfonamide. MS (M–1) @190 oil
11. 13514-006 N-Isopropyl-p-nitrobenzenesulfonamide. MS $M^+$ @ 244. $M_p$ 113°–114° C.
12. 13514-025 N-Butyl-2,4,6-trimethylbenzenesulfonamide. MS $M^+$ @ 255. $M_p$ 45° C.
13. 13514-026 N-Butyl-2,4,6,-triisopropylbenzenesulfonamide. MS $M^+$ @ 339. $M_p$ 104° C.
14. 13514-032 Benzyl 6-(N-tosylamino)-hexanoate. MS $M^+$ @ 375 oil
15. 13514-057 t-Butyl N-tosyl-β-alanine. MS $M^+$ @ 242 (M–57) oil
16. 13514-058 Benzyl 5-(N-tosylamino)-pentanoate MS $M^+$ @ 361 oil.
17. 13513-170 N-Butyl-p-toluenesulfonamide. MS $M^+$ @ 227. $M_p$ 42°–44° C.
18. 13513-173 N-Butyl-p-bromobenzenesulfonamide. MS $M^+$ @ 241. $M_p$ 53°–54° C.
19. 13513-172 N-Butyl-o-nitrobenzenesulfonamide. MS $M^+$ @ 258. $M_p$ 58°–60° C.
20. 13513-174 N-Butyl-p-nitrobenzenesulfonamide. MS $M^+$ @ 258. $M_p$ 80°–81° C.
21. 13513-213 N-Butyl-2,4-dinitrobenzene sulfonamide. MS $M^+$ @ 304. $M_p$ 60°–62° C.
22. 13513-085 Benzyl 6-(N-trifluoromethylsulfonylamino)-hexanoate oil
23. 13513-083 Benzyl N-(trifluoromethylsulfonyl)-4-(carboxymethyl) aniline
24. 14973-1A Benzyl N-(5-carboxypentyl)-p-bromobenzenesulfonamide. MS $M^+$ @ 439. $M_p$ 52°–56° C.
25. 14973-37A Benzyl N-(5-carboxypentyl)-p-nitrobenzenesulfonamide. MS $M^+$ @ 406. $M_p$ 86°–88° C.

EXAMPLE 2

Preparation of N-sulfonyl-9-acridinecarboxamides

Freshly sublimed potassium tert-butoxide (200 mole percent) and tri-n-butylbenzylammonium bromide (1 mole percent) were suspended in toluene under nitrogen. A selected sulfonamide (200 mole percent) was added, the mixture was stirred for 10–30 minutes before evaporating to dryness and the dried material resuspended in the solvent. [Alternatively, the phase transfer catalyst may be omitted and an appropriate anion may be generated in tetrahydrofuran.] After the addition of 9-chlorocarbonylacridine hydrochloride (100 mole percent), the reaction mixture was stirred for 3 to 14 hours at room temperature until no further change was noted by thin-layer chromatography ("TLC"). The reaction solution was diluted with ethyl ether (10 volumes) and washed with brine (25 ml). After drying over $MgSO_4$, filtering and evaporating, the crude product was chromatographed (on a Chromatotron™ chromatograph [available from Harrison Research, Palo Alto, Calif.] using a 2 mm silica rotor and employing an ethylacetate/hexane gradient). The fractions containing the product were collected, evaporated and crystallized from ether/heptane (i.e., the fractions were dissolved in ether followed by the addition of heptane until the mixture became cloudy).

The following compounds were prepared from starting materials as indicated in brackets wherein starting materials prepared herein are identified by the number associated with them in Example 1 or in this example, and wherein a commercial source is provided in brackets for each identified starting material not synthesized-herein. All other notations are explained in Example 1.

26. 13513-234 N-Phenyl-N-p-toluenesulfonyl-9-acridinecarboxamide [compound 1]. MS $M^+$ @ 452. $M_p$ 200° C.
27. 13513-236 N-Phenyl-N-p-bromobenzenesulfonyl 9-acridinecarboxamide [compound 2]. MS $M^+$ @ 516. $M_p$ 218°–219° C.
28. 13513-240 N-Phenyl-N-o-nitrobenzenesulfonyl 9-acridinecarboxamide [compound 3]. MS $M^+$ @ 483. $M_p$ 197°–200° C.
29. 13513-242 N-Phenyl-N-p-nitrobenzenesulfonyl-9-acridinecarboxamide [compound 4]. MS $M^+$ @ 483
30. 13513-243 N-Phenyl-N-trifluoromethanesulfonyl-9-acridinecarboxamide [compound 6]. MS $M^+$ @ 430. $M_p$ 162° C.
31. 13514-007 N-Isopropyl-N-p-toluenesulfonyl-9-acridinecarboxamide [compound 7]. MS $M^+$ @ 418. $M_p$ 163°–164° C.
32. 13514-009 N-Isopropropyl-N-p-bromobenzenesulfonyl-9-acridinecarboxamide [compound 8]. MS $M^+$ @ 482. $M_p$ 205° C.
33. 13514-012 N-Isopropyl-N-o-nitrobenzenesulfonyl-9-acridinecarboxamide [compound 9]. MS $M^+$ @ 449. $M_p$ 215° C.
34. 13514-001 N-Isopropyl-N-trifluoromethane sulfonyl-9-acridinecarboxamide [compound 10]. MS $M^+$ @ 396

35. 13514-028 N-Butyl-N-2,4,6,-trimethylbenzenesulfonyl-9-acridinecarboxamide [compound 12]. MS M$^+$ @ 460. M$_p$ 88°–90° C.
36. 13514-031 N-Butyl-2,4,6-triisopropylbenzenesulfonyl-9-acridinecarboxamide [compound 13]. MS M$^+$ @ 544
37. 13514-042 Benzyl N-tosyl-N-(5-carboxypentyl)-9-acridinecarboxamide [compound 14]. MS M$^+$ @ 550 oil
38. 13514-062 Benzyl N-tosyl-N-(4-carboxybutyl)-9-acridinecarboxamide [compound 16]. MS M$^+$@566
39. 13514-069 t-Butyl N-tosyl-N-(2-carboxyethyl)-9-acridinecarboxamide [compound 15]. MS M$^+$ 504. M$_p$ 157°–158° C.
40. 13513-186 N-Butyl-N-p-toluenesulfonyl-9-acridinecarboxamide [compound 17]. MS M$^+$ @ 432. M$_p$ 122°–123° C.
41. 13513-191 N-Butyl-N-o-nitrophenylsulfonyl-9-acridinecarboxamide [compound 19]. MS M$^+$ @ 463. M$_p$ 170° C.
42. 13513-195 N-Butyl-N-p-nitrophenylsulfonyl-9-acridinecarboxamide [compound 20]. MS M$^+$ 463. M$_p$ 210° C.
43. 13513-218 N-Butyl-N-(2,4-dinitrophenylsulfonyl)-9-acridinecarboxamide [compound 21]. MS M$^+$ @ 508. M$_p$ 95° C.
44. 14973-9C Benzyl N-(5-carboxypentyl)-N-p-bromobenzenesulfonyl-9-acridinecarboxamide [compound 24]. MS (M+H) @ 645
45. 14973-40C Benzyl N-(5-carboxypentyl)-N-p-nitrobenzenesulfonyl-9-acridinecarboxamide [compound 25]. MS (M+H) @ 645
46. 14973-88A N-p-Toluenesulfonyl-9-acridinecarboxamide [p-toluene sulfonamide (Aldrich)]. M$_p$ 276° C.
47. 14973-21C N-Allyl-N-p-toluenesulfonyl-9-acridinecarboxamide [compound 46]. M$_p$ 136°–138° C.
48. 13513-202 N-Butyl-N-p-bromobenzenesulfonyl-9-acridinecarboxamide. MS M$^+$ @ 496/498. M$_p$ 148°–149° C.

EXAMPLE 3

Preparation of 10-Methyl N-sulfonylacridinium Carboxamides

Methylation of N-sulfonylacridine carboxamides was performed according to the following procedure. Each acridine sulfonamide was dissolved in anydrous methylene chloride. Anhydrous Na$_2$CO$_3$ (5×weight of the sulfonimide) was added followed by methyl triflate (20×weight of the sulfonamide). The suspension was stirred under nitrogen for 14–48 hours at room temperature to 40° C. The reaction was monitored by TLC (reverse phase). The product was obtained after filtration and evaporation of the solvent and of excess methyl triflate. Purification was achieved by triturating the solid residue with hot benzene or by reverse phase HPLC.

The following compounds were prepared, and they are described according to the numerals, symbols and abbreviations which are explained in Example 1 or in Example 2.

49. 13513-246 10-Methyl-N-phenyl-N-p-toluenesulfonyl-9-acridinium carboxamide trifluoromethanesulfonate [compound 26]. MS M$^+$ @ 467. M$_p$ 210°–24° C. (decomp.)
50. 13513-247 10-Methyl-N-phenyl-N-p-bromobenzenesulfonyl-9-acridinium carboxamide trifluoromethanesulfonate [compound 27]. MS M$^+$ @ 531, 533. M$_p$ 240° C. (decomp.)
51. 13513-248 10-Methyl-N-phenyl-o-nitrobenzenesulfonyl-9-acridinium carboxamide trifluoromethanesulfonate [compound 28]. MS M$^+$ @ 490. M$_p$ 248°–50° C. (decomp.)
52. 13513-249 10-Methyl-N-phenyl-N-trifluoromethanesufonyl-9-acridinium carboxamide trifluoromethanesulfonate [compound 30]. MS M$^+$ @ 445
53. 13513-250 10-Methyl-N-phenyl-p-nitrobenzenesulfonyl-9-acridinium carboxamide trifluoromethanesulfonate [compound 29]. MS M$^+$ @ 484
54. 13514-013 10-Methyl-N-isopropyl-N-p-toluenesulfonyl-9-acridinium carboxamide trifluoromethanesulfonate [compound 31]. MS M$^+$ @ 433. M$_p$ 214° C.
55. 13514-014 10-Methyl-N-isopropyl-N-p-bromobenzenesulfonyl-9-acridinium carboxamide trifluoromethanesulfonate [compound 32]. MS M$^+$ @ 497/499. M$_p$ 200° C. (decomp)
56. 13514-018 10-Methyl-N-isopropyl-N-o-nitrobenzenesulfonyl-9-acridinium carboxamide trifluoromethanesulfonate [compound 33]. MS M$^+$ @ 464
57. 13514-021 10-Methyl-N-isopropyl-N-trifluoromethanesulfonyl-9-acridinium carboxamide trilluormethanesulfonate [compound 34]. MS M$^+$ @ 411
58. 13514-037 10-Methyl-N-butyl-N-(2,4,6-trimethylbenzenesulfonyl-9-acridinium carboxamide trifluoromethanesulfonate [compound 35]. MS M$^+$ @ 475. M$_p$ 227° C. (decomp.)
59. 13514-038 10-Methyl-N-butyl-N-(2,4,6-triisopropylbenzenesulfonyl-9-acridinium carboxamide trifluoromethanesulfonate [compound 36]. MS M$^+$ @ 559. M$_p$ 231° C. (decomp.)
60. 13514-044 Benzyl 10-methyl-N-tosyl-N-(5-carboxypentyl)-9-acridinium carboxamide trifluoromethanesulfonate [compound 37]
61. 13514-079 t-Butyl 10-methyl-N-tosyl-N-(2-carboxyethyl)-9-acridinium carboxamide trifluoromethanesulfonate [compound 39]. MS M$^+$ @ 519. M$_p$ 207° C. (decomp.)
62. 13513-211 10-Methyl-N-butyl-N-p-toluenesulfonyl-9-acridinium carboxamide trifluoromethanesulfonate. [compound 40]. MS M$^+$ @ 447
63. 13513-212 10-Methyl-N-butyl-N-p-bromobenzenesulfonyl-9-acridinium carboxamide trifluoromethanesulfonate [compound 48]. MS M$^+$ @ 511. M$_p$ 126° C.
64. 13513-215 10-Methyl-N-butyl-N-o-nitrophenylsulfonyl-9-acridinium carboxamide trifluoromethanesulfonate [compound 41]. MS M$^+$ @ 478. M$_p$ 232°–234° C.
65. 13513-216 10-Methyl-N-butyl-N-p-nitrophenysulfonyl-9-acridinium carboxamide trifluoromethanesulfonate [compound 42]. MS M$^+$ @ 478. M$_p$ 201° C.
66. 13513-230 10-Methyl-N-butyl-N-(2-4 dinitrophenylsulfonyl)-9-acridinium carboxamide trifluoromethanesulfonate [compound 43]. MS M$^+$ @ 523. M$_p$ 215°–220° C.
67. 14973-31B 10-Methyl-N-allyl-N-p-toluenesulfonyl-9-acridinium carboxamide trifluoromethanesulfonate [compound 47]. MS M+2 @433
68. 14973-47A Benzyl 10-methyl-N-(5-carboxypentyl)-N-p-nitrobenzenesulfonyl-9-acridinium carboxamide trifluoromethanesulfonate [compound 45]. MS M$^+$ @ 626. M$_p$ 139°–141° C.
69. 14973-90A 10-Methyl-N-methyl-N-p-toluenesulfonyl-9-acridinium carboxamide trifluoromethanesulfonate [compound 46]. MS M$^+$ @ 405
70. 14973-25A Benzyl 10-methyl-N-(5-carboxypentyl)-N-(o-bromobenzenesulfonyl)-9-acridinium carboxamide [compound 44]

EXAMPLE 4

Synthesis of 10-methyl-N-tosyl-N-(6-hexanoyl-N-hydroxysuccinimido)-9-acridinium Carboxamide Trifluoromethanesulfonate Compound 37 (450 mg, 0.78 moles) was treated with ml of 31% HBr in acetic acid at 50° C. for 2 hours under $N_2$. The solution was poured into 30 ml of water and cooled. Carboxylic acid compound 71, 13514-045 [N-tosyl-N-(5-carboxypentyl)-9-acridinecarboxamide] was separated by filtration.

Compound 71 (100 mg., 0.2 mmol) was dissolved in dry methylene chloride (5 ml) and treated with N-hydroxysuccinimide (23 mg, 0.2 mmol) and dicyclohexylcarbodiimide (41 mg) under $N_2$ for 12 hours. After reacting, the solution was filtered and then evaporated to dryness to yield an active ester, compound 72, 13514-052 [N-tosyl-N-(6-hexanoyl-N-hydroxysuccinimido)-9-acridinecarboxamide].

Compound 72 was methylated as in Example 3 to give compound 73. Compounds 71, 72, and 73 are described below using the numerals, symbols and abbreviations which are explained in Example 1.

71. 13514-045 N-Tosyl-N-(5-carboxypentyl)-9-acridinecarboxamide [compound 37]. MS $M^+$ @ 240. $M_p$ 150°–152° C.
72. 13514-052 N-Tosyl-N-(6-hexanoyl-N-hydroxysuccinimido)-9-acridinecarboxamide [compound 71]. MS $M^+$ @ 588
73. 13514-054 10-Methyl-N-tosyl-N-(6-hexanoyl-N-hydroxysuccinimido)-9-acridinumcarboxamide trifluoromethanesulfonate [compound 72]

EXAMPLE 5

Synthesis of 10-Methyl-N-tosyl-N-(5-pentanoyl-N-hydroxysuccininimido)-9-acridinium Carboxamide Trifluoromethanesulfonate Compound 38, 13514-062, was treated as in Example 4 and yielded compound 74, 13514-065 [N-tosyl-N-(4-carboxybutyl)-9-acridinecarboxamide].

Compound 74 was coupled to N-hydroxysuccinimide, as in Example 4, to give compound 75, 13514-067, N-tosyl-N-(5-pentanoyl-N-hydroxysuccinimido)-9-acridinecarboxamide. This compound was methylated as in Example 3 to give compound 76, 13514-078 [10-methyl N-tosyl-N-(5-pentanoyl-N-hydroxysuccinimide)-9-acridinium carboxamide trifluoromethanesulfonate].

Compounds 74, 75 and 76 are described using the numerals, symbols and abbreviations which are explained in Example 1.

74. 13514-065 N-Tosyl-N-(4-carboxybutyl)-9-acridinecarboxamide. MS $M^+$ @ 476. $M_p$ 152°–155° C.
75. 13514-067 N-Tosyl-(5-pentanoyl N-hydroxy succinimido)-9-acridinecarboxamide [compound 74]. MS $M^+$ @ 573
76. 13514-078 10-Methyl-N-tosyl-N-(5-pentanoyl-N-hydroxysuccinimido)-9-acridinium carboxamide trifluoromethanesulfonate [compound 75]

EXAMPLE 6

Synthesis of 10-methyl-N-tosyl-N-(2-carboxyethyl-9-acridinium Carboxamide Trifluoromethanesulfonate Compound 61, 13514-079 (50 mg, 0.072 mmol) was dissolved in 2 ml of trifluoroacetic acid ["TFA"] at 0° C. under $N_2$. After stirring for 15 minutes, the TFA was evaporated and the residue was recrystallized from methanol/ether (i.e., the residue was dissolved in methanol, adding ether until cloudy). Alternatively, compound 61, was refluxed in 1N HCl for 3 hours. The aqueous solution was evaporated to dryness to leave a residue, and the residue was purified by preparative reverse phase HPLC. Compound 77, 13514-081 [10-methyl N-tosyl-N-(2-carboxyethyl)-9-acridinium carboxamide] resulted from either approach. Compound 77 is described using the numerals, symbols and abbreviations which are explained in Example 1.

77. 13514-081 10-Methyl-N-tosyl-N-(2-carboxyethyl)-9-acridinium carboxamide trifluoromethanesulfonate [compound 61]. MS (M+14) @477; $M^+$ @ 463. $M_p$ 227° C. (decomp.)

EXAMPLE 7

Preparation of Acridinecarboxamides

An amine (110 mole percent) and triethylamine (220 mole percent) were dissolved in methylene chloride. One hundred mole percent of 9-chlorocarbonyl acridine was added dropwise as a solution in methylene chloride. The reaction was stirred under $N_2$ for 3 hours. The solution was filtered through silica gel and the filtrate was evaporated to leave a residue. The residue was then recrystallized from an appropriate solvent (isopropyl ether for compound 78 and ethyl ether for compound 79).

The following amides were prepared, and are described using the numerals, symbols and abbreviations which are explained in Example 1.

78. 14973-15A N-Allyl-9-acridinecarboxamide [Allyl amine (Aldrich)]. MS $M^+$ @ 262. $M_p$ 192° C.
79. 14973-6A Benzyl N-(5-carboxypentyl)-9-acridinecarboxamide [6-Amino caproic acid (Aldrich)]. MS $M^+$ @ 458. $M_p$ 86° C.

EXAMPLE 8

Synthesis of Acridinium Carboxamides

An ester (either compound 44 or compound 68) was added to a 1N HCl solution and refluxed for 3–4 hours. Upon cooling, the suspension was either filtered and the product collected, or the suspension was extracted with a chloroform:isopropanol (3:2) mixture, which provided the desired product (compound 80 or 81, respectively) on evaporation. Compounds 80 and 81 are described using the numerals, symbols and abbreviations which are explained in Example 1.

80. 14379-27A 10-Methyl-N-(5-carboxypentyl)-N-p-bromobenzenesulfonyl-9-acridinium carboxamide trifluoromethanesulfonate [compound 44]. MS $M^+$ @ 569, 571. $M_p$ 148°–150° C.
81. 14973-51A 10-Methyl-N-(5-carboxypentyl)-N-p-nitrobenzenesulfonyl-9-acridinium carboxamide trifluoromethanesulfonate [compound 68]. MS $M^+$ @ 536

EXAMPLE 9

Synthesis of 10-(3-sulfopropyl)-N-tosyl-N-(2-carboxyethyl)-9-acridinium Carboxamide Propane sultone (260 mole percent) was heated with t-butyl N-tosyl-N-(2-carboxyethyl)-9-acridinecarboxamide (compound 39, 13514-069) at 110°–120° C. for 2 hours. After cooling, the solid mass was taken up in methanol and filtered. The filtrate was evaporated to dryness and the residue triturated with benzene to remove un-quaternized material.

The crude product compound was treated with trifluoracetic acid at 0° C. then allowed to warm to 25° C. over a period of 15 minutes. The residue obtained upon evaporation was purified chromatographically on preparative thick-layer chromatography plates (C-18 PLKC 18F, 20×20 cm, 1000M, as available from Whatman, Clifton, N.J.), eluted with 70 parts methanol/30 parts 0.5% aqueous acetic acid, and further purified by ion exchange on Cellex-D™ resin [BioRad Laboratories, Richmond, Calif.] using 8% formic acid to elute the product, compound 82, which is described below using the numerals, symbols and abbreviations which are explained in Example 1.

82. 14496-243 10-(3-sulfopropyl)-N-tosyl-N-(2-carboxyethyl)-9-acridinium carboxamide [compound 39]. MS M$^+$ @ 572

EXAMPLE 10

Synthesis of 10-(3-sulfopropyl)-N-tosyl-N-(3-sulfopropyl)-9-acridinium Carboxamide Fifty milligrams of N-tosyl-9-acridinecarboxamide (compound 46, 14973-88A) were heated at 140°–150° C. under argon in a sealed tube with 500 mg of propane sultone for 3 hours. After cooling, excess propane sultone was removed by trituration with benzene (5 ml×3). The crude product was purified by anion exchange chromatography using BioRad AG-1-X4 formate form [BioRad Laboratory, Richmond, Calif.], eluted with a gradient of aqueous formic acid. The product, compound 83, is described below using the numerals, symbols and abbreviations explained in Example 1.

83. 30253-020 10-(3-Sulfopropyl)-N-tosyl-N-(3-sulfopropyl)-9-acridinium carboxamide. [compound 46]. MS M+H @ 621.

EXAMPLE 11

Evaluation of N-sulfonylacridinium Carboxamide Chemiluminescence

Acridinium compounds to be tested for chemiluminescence were dissolved in dimethyl formamide ("DMF") and then diluted with 0.05M sodium citrate (pH 5.0) or 0.05M sodium phosphate (pH 7.0) buffer to give solutions of about 3×10$^{-9}$M. Twenty microliters of each buffered solution was diluted with 300 μl of 0.1N HCl and chemiluminscence was triggered with 150 μl of 0.03% H$_2$O$_2$ in 0.2N NaOH.

The light generated was recorded on a photon counter luminometer over a 10 second interval except where a longer interval is indicated in Table 1. The specific activity of each compound is provided in the form of counts/mole in Table 1.

TABLE 2

| Compound No. | Identifying No. | Counts/Mole |
|---|---|---|
| 49 | 13513-246 | 9.4 × 10$^{18}$ |
| 50 | 13513-247 | 9 × 10$^{18}$ |
| 51 | 13513-248 | 1 × 10$^{19}$ |
| 50 | 13513-249 | 1.2 × 10$^{19}$ |
| 53 | 13513-250 | 1 × 10$^{19}$ |
| 54 | 13514-013 | 8.3 × 10$^{18}$ |
| 55 | 13514-014 | 1.25 × 10$^{19}$ |
| 56 | 13514-018 | 1.1 × 10$^{19}$ |
| 57 | 13514-021 | 1.5 × 10$^{19}$ |
| 58 | 13514-037 | 5.2 × 10$^{18}$ (50 secs) |
| 59 | 13514-038 | 1.4 × 10$^{19}$ |

TABLE 2-continued

| Compound No. | Identifying No. | Counts/Mole |
|---|---|---|
|  |  | (20 secs) |
| 62 | 13513-211 | 5 × 10$^{18}$ |
| 63 | 13513-212 | 7 × 10$^{18}$ |
| 64 | 13513-215 | 6.1 × 10$^{18}$ |
| 65 | 13513-216 | 8 × 10$^{18}$ |
| 66 | 13513-230 | 5 × 10$^{18}$ |

EXAMPLE 12

Stability Test of Compound 62 (13513-211)

Compound 62 (2 mg) was dissolved in 1 ml of methanol. Fifty microliters of this solution were added to each of the following buffers:

1) 500 microliters of 0.05M sodium phosphate, pH 5.0
2) 500 microliters of 0.05M sodium phosphate, pH 5.5
3) 500 microliters of 0.05M sodium phosphate, pH 6.0
4) 500 microliters of 0.05M sodium phosphate, pH 6.5
5) 500 microliters of 0.05M sodium phosphate, pH 7.0.

Each solution was analyzed on a Perkin-Elmer Series 4 HPLC using a reverse phase column (C-18 μ Bondapak, 3.9 mm×30 cm, available from Waters Associates, Milford, Mass.). The elution was done with 75% methanol and 25% 5 mM pentanesulfonic acid in 1% aqueous acetic acid at a flow rate of 1 ml/min. The effluent was monitored at 254 nm.

After 4 weeks at room temperature, the solutions at pH 5.0, pH 5.5 and pH 6.0 showed no sign of decomposition, while at pH 6.5 and at pH 7.0, 20% and 70% decomposition were seen, respectively.

EXAMPLE 13

Comparison of Temperature and pH Stabilities of Acridinium Compounds in Buffer at pH 7.2

Three different acridinium compounds, compound 62, 13513-211, a compound identified by the number 13514-020 [4-(carbobenzyloxymethyl)-phenyl-10-methyl-9-acridinium carboxylate trifluoromethanesulfonate (compound 87] as prepared as in Weeks, et al., Clin. Chem., 29, 1474–79 (1983), and compound 83, 30253-020, were compared for temperature and pH stability. The comparison was carried out in methanol or water at a concentration of 1.0 mg/ml (which is approximately equivalent to 1.6×10$^{-3}$M). Each of the samples was diluted 1:100 in an acid solution containing one part of 0.1N HCl plus one part phosphate-buffered saline ("PBS") pH 6.8 with 0.01% Tween 20® (polyoxyethylenesorbitan monolaurate available from Sigma Chemical Company, St. Louis, Mo.). The final pH of the diluent solution were about 1.5. The molarity of each of these solutions was 1.6×10$^{-5}$M.

Each of the solutions was scanned to record a UV-visible absorption spectrum in order to determine molar extinction coefficients and in order to detect any appreciable differences in the absorbance spectra. The UV-visible absorption spectra of these acridinium compounds have the characteristics presented in Table 2.

TABLE 3

| Compound No. | Identifying No. | Wavelength | Observed Absorbance |
|---|---|---|---|
| 62 | 13513-211 | 263 nm | 1.40 |
|  |  | 369 nm | 0.286 |
| 83 | 30253-020 | 263.5 nm | 1.42 |
|  |  | 370 nm | 0.304 |
| 87 | 13514-020 | 262 nm | 1.72 |
|  |  | 368 nm | 0.334 |

For all three compounds, $\epsilon_{370} \cong 18,000$ and $\epsilon_{263} \cong 87,000$.

These spectra indicate that there is very little difference either in UV-visible absorbance or in molar extinction coefficients among these three compounds. In fact, within the limitations of experimental error, few or no spectral differences were observed.

The $1.6 \times 10^{-5}$M stock solutions of the three compounds were serially diluted 10-fold in 0.01M sodium phosphate with 0.05% normal human serum at pH 4.8. They were also serially diluted 10-fold in PBS (pH 7.2) with 0.01% Tween 20®.

Because it is known that, in general, acridinium compounds are more stable at an acid pH, it was assumed that the counts obtained from the samples diluted in pH 4.8 buffer would be representative of the maximum stability with maximum chemiluminescent output. All three compounds were serially diluted 10-fold to a final concentration of $1.6 \times 10^{-10}$M. A 10 µl aliquot of each sample was added to 90 µl of 0.05N HCl. Chemiluminescence was triggered with 200 µl of 0.03% $H_2O_2$ in 0.25N NaOH and counts were monitored on luminometer for 6 seconds with results as presented in Table 3. Results are presented in Table 3 for each of three runs.

TABLE 4

| Compound No. | Identifying No. | Counts/6 Seconds |
|---|---|---|
| 62 | 13513-211 | 92,669 |
|  |  | 91,241 |
|  |  | 91,995 |
| 83 | 30253-020 | 138,791 |
|  |  | 141,962 |
|  |  | 145,133 |
| 87 | 13514-020 | 59,438 |
|  |  | 59,443 |
|  |  | 59,449 |

Within experimental error, chemiluminescent output on the luminometer did not differ among the compounds, as indicated in Table 4.

TABLE 5

Chemiluminescent Output at pH 4.8

| Compound No. | Identifying No. | Counts/Mole |
|---|---|---|
| 62 | 13513-211 | $5.7 \times 10^{19}$ |
| 83 | 30253-020 | $8.7 \times 10^{19}$ |
| 87 | 13514-020 | $3.7 \times 10^{19}$ |

When 10 µl of these same compounds were diluted to $1.6 \times 10^{-10}$M in 90 µl PBS buffer (pH 7.2) with 0.01% Tween 20® and not acidified prior to running chemiluminescence output determinations as above, the results were somewhat different, especially for the acridinium carboxylate compound 13514-020, as shown in Table 5. Results are presented in Table 5 for each of three runs.

TABLE 6

Chemiluminescent Output at pH 7.2

| Compound No. | Identifying No. | Counts/6 Seconds |
|---|---|---|
| 62 | 13513-211 | 88,633 |
|  |  | 89,135 |
|  |  | 90,394 |
| 83 | 30253-020 | 133,560 |
|  |  | 137,929 |
|  |  | 142,299 |
| 87 | 13514-020 | 8,185 |
|  |  | 7,274 |
|  |  | 6,363 |

The compound identified by the number 13514-020 produced only $4.4 \times 10^{18}$ counts/mole in pH 7.2 buffer, almost an order of magnitude fewer counts than it produced at pH 4.8. This may be due to pseudobase formation by a large proportion of the molecules at the more alkaline pH, the pseudobase being substantially less chemiluminescent than the corresponding positively charged acridinium compound.

The N-sulfonylacridinium carboxamide compounds showed only a very small drop in counts when incubated at pH 7.2. This suggests that they do not undergo pseudobase formation to any appreciable degree, at least at this pH.

The dilution series of all three of the acridinium compounds in pH 7.2 buffer were stored overnight at room temperature and then assayed. Both N-sulfonylacridium carboxamide compounds showed virtually no change in chemiluminescence. The phenyl acridinium carboxylate showed a significant drop after 20 hours at room temperature.

The samples were then placed in an incubator at 45° C. Every day for the duration of the study they were removed from the incubator, cooled to room temperature, and 10 µl aliquots diluted into 90 µl of PBS buffer (pH 7.2) were assayed for chemiluminescence.

Neither of the N-sulfonylacridinium carboxamides showed any significant difference in chemiluminescent output when diluted either in 0.05N HCl or in PBS at pH 7.2. However, the acridinium carboxylate 13514-020 exhibited a significantly different chemiluminescent output when diluted in 0.05N HCl or in PBS buffer at pH 7.2. When diluted in PBS buffer (pH 7.2), the acridinium carboxylate consistently produced at least 10-fold fewer counts than when diluted in 0.05N HCl.

The 10,N-bis-(3-sulfopropyl) acridinium carboxamide (compound 83, 30253-020) appears to be quite stable at pH 7.2 at 45° C. After 10 days under such conditions no appreciable loss of chemiluminescence was observed. Compound 13513-211 produced 10-fold fewer counts, and the acridinium carboxylate 13514-020 produced $10^3$ fewer counts under the same conditions.

EXAMPLE 14

Preparation of Labeled IgG

Disulfopropyl compound 83, 30253-020, was activated by treatment with phosphorous oxychloride in acetonitrile at 45° C. for 12 hours under argon. The solvent and excess $POCl_3$ were removed in vacuo and the activated compound was used directly in the labeling reaction.

Thus, 10 mg of rabbit IgG (Sigma Chemical Company, St. Louis, Mo.) was dissolved in 0.1M sodium phosphate buffer (2 ml, pH 7.0) containing 1% Tween 80® (polyoxyethylenesorbitan monooleate, available from Sigmal Chemical Co. St. Louis, Mo.). One ml of this solution was mixed with about 2 mg of the bis-sulfonylchloride. The solution was agitated periodically by sonication and stirring for one hour at room temperature.

An aliquot (0.5 ml) of the reaction solution was chromotographed over Sephadex® G-25 (beads for gel filtration, prepared by cross-linking dextran with epichlorohydrin, 10 cm×0.75 cm), as available from Pharmacia, Piscataway, N.J., and eluted with 0.1M phosphate buffer (pH 6.5).

The labeled protein eluted as a weakly green fluorescent band. The labeled protein was further purified by HPLC using a Bio-Sil® TSK-250 column (size exclusion column, hydrophilic bonded phase silica BioRad, Richmond, Calif.). The resulting conjugate (30253-34) contained 0.8 labels/protein, as determined from the ratio of the absorbance at 370 nm ($\epsilon \cong 10,000$, acridinium salt) to the absorbance 280 nm ($\epsilon \cong 210,000$, IgG).

EXAMPLE 15

Heat Stability Studies

The conjugate 30253-34, as synthesized in Example 14, was serially diluted 10-fold in three buffers (0.1M sodium phosphate, 0.01% Tween 20®, pH 6.3; 0.01M sodium phosphate, 0.15M NaCl, 0.01% Tween 20®, pH 6.8; and 0.01M sodium phosphate, 0.15M NaCl, 0.01% Tween 20®, pH 7.2) to a concentration of $2 \times 10^{-9}$M IgG and $1.6 \times 10^{-9}$M acridinium. A dilution series was prepared and initial counts were recorded by taking 10 µl of the sample, diluting with 90 µl of PBS buffer at pH 6.3, pH 6.8, or pH 7.2, and then triggering chemiluminescence with 200 µl of 0.03% $H_2O_2$ in 0.25N NaOH. A 100 µl sample of PBS buffer was used as a control for each series.

Counts shown in Table 6 are averages of results for duplicate samples assayed on the day on which the dilution series was prepared. The concentration shown in Table 5 is the concentration of the sample prior to dilution. The amount in parentheses for each entry in Table 5 is the amount of conjugate present in the sample.

TABLE 7

| Concentration (Amount) | | Counts/6 Seconds |
|---|---|---|
| pH 6.3 | | |
| buffer | (0 moles) | 253 |
| $2 \times 10^{-10}$M | ($2 \times 10^{-14}$ moles) | 216,054 |
| $1 \times 10^{-10}$M | ($1 \times 10^{-14}$ moles) | 100,842 |
| $5 \times 10^{-11}$M | ($5 \times 10^{-15}$ moles) | 48,704 |
| $2.5 \times 10^{-11}$M | ($2.5 \times 10^{-15}$ moles) | 23,771 |
| $1.25 \times 10^{-11}$M | ($1.25 \times 10^{-15}$ moles) | 11,475 |
| $6 \times 10^{-12}$M | ($6 \times 10^{-16}$ moles) | 5,866 |
| pH 6.8 | | |
| buffer | (0 moles) | 233 |
| $2 \times 10^{-10}$M | ($2 \times 10^{-14}$ moles) | 295,608 |
| $1 \times 10^{-10}$M | ($1 \times 10^{-14}$ moles) | 149,725 |
| $5 \times 10^{-11}$M | ($5 \times 10^{-15}$ moles) | 76,820 |
| $2.5 \times 10^{-11}$M | ($2.5 \times 10^{-15}$ moles) | 38,801 |
| $1.25 \times 10^{-11}$M | ($1.25 \times 10^{-15}$ moles) | 18,408 |
| $6 \times 10^{-12}$M | ($6 \times 10^{-16}$ moles) | 9,398 |
| pH 7.2 | | |
| buffer | (0 moles) | 726 |
| $2 \times 10^{-10}$M | ($2 \times 10^{-14}$ moles) | 309,445 |
| $1 \times 10^{-10}$M | ($1 \times 10^{-14}$ moles) | 156,311 |
| $5 \times 10^{-11}$M | ($5 \times 10^{-15}$ moles) | 77,238 |
| $2.5 \times 10^{-11}$M | ($2.5 \times 10^{-15}$ moles) | 39,879 |
| $1.25 \times 10^{-11}$M | ($1.25 \times 10^{-15}$ moles) | 19,925 |
| $6 \times 10^{-12}$M | ($6 \times 10^{-16}$ moles) | 10,526 |

Each dilution series was placed in a warm air incubator at 45° C. after an initial reading was taken. A duplicate reading was made on each sample daily and then the readings were averaged.

When the conjugate was stored at pH 6.8 and at 45° C., there was no loss in chemiluminescent activity of the label over a 15 day period of observation, at any dilution. Essentially the same results were observed when the conjugate was stored in PBS buffer at pH 7.2.

EXAMPLE 16

Comparison of CLIA vs. RIA

A. Preparation of Acridinium-Labeled Anti-HsAg Conjugate. Compound 75 (13514-081, Example 6) (12.5 µmol) was dissolved in 200 µl of DMF, was treated with NHS (dissolved in 50 µl of DMF) and dicyclohexylcarbodiimide (dissolved in 50 µl of DMF) ("DCC"); and stirred for 12 hours at room temperature. The solution of the activated ester was mixed with mouse monoclonal anti-HBsAg in 0.1M sodium phosphate buffer (pH 6.3) in a molar ratio of 100:1 at 4° C. for 12 hours.

The conjugate was then dialysed against PBS buffer, pH 6.3, until the absorbance of the dialysate indicated no free label. A UV spectral analysis indicated between 2 to 6 labels/antibody (as determined from a ratio of absorbances as in Example 14).

B. Assay for HBsAg. Either type $A_d$ or type $A_y$ HBsAg (200 µl) was diluted in calf serum and was reacted with an Auszyme™ (Abbott Laboratories, Abbott Park, Ill.) monoclonal antibody bead and $2 \times 10^5$ of counts of $^{125}$I-labeled mouse monoclonal anti-HBsAg antibody (40 µl, in the RIA) or an acridinium-labeled mouse monoclonal anti-HBsAg antibody (40 µl, in the CLIA). in PBS containing 50% calf serum, 10% human serum, 0.05% Tween 20® and 5 mM EDTA (pH 6.3), for three hours at 40° C. The beads were then washed 6 times in water and counted for their activities. Calf serum was used as a negative control.

In the CLIA, a polystyrene bead with conjugate bound adsorbed thereto was mixed with 250 µl phosphate, 0.5 mM, pH 5.3, in a glass vial suitable for use in a luminometer. While the sample was in the measuring position, 0.2 ml of 0.03% $H_2O_2$ in 0.25N NaOH was then injected into the glass vial. The light emmitted was measured in the luminometer. Reading began 0.012 seconds before initiation of the chemical reaction and continued for 6 seconds.

The results are presented in Table 7.

TABLE 8

| Concentration | CLIA | | RIA | |
|---|---|---|---|---|
| (ng/ml) | $A_d$ | $A_y$ | $A_d$ | $A_y$ |
| 1.0 | 2214 | 3144 | 371 | 400 |
| 0.5 | 1256 | 2494 | 236 | 408 |
| 0.25 | 701 | 921 | 221 | 248 |
| 0.125 | 521 | 592 | 173 | 179 |
| Calf Serum | 151 | 179 | | |
| Cut-off | 327 | 376 | | |

Under the stated conditions, the sensitivity for the CLIA was less than 0.125 ng/ml for both the $A_d$ and $A_y$ types of HBsAg. For the RIA the sensitivity was 1.0 ng/ml for both the $A_d$ and $A_y$ types. The cut-off count was 2.1 times that of the negative control.

Table 8 clearly shows that chemiluminescent immunoassays according to the present invention are more sensitive than comparable radioimmunoassays.

EXAMPLE 17

A Comparison of CLIA and EIA

A. Preparation of labeled anti-hTSH (30234-207). Compound 75 (13514-081, Example 6) (2 mg, 4.3 µmoles) in 200 ml of acetonitrile was treated with 1-ethyl-3-(3-dimethylaminopropyl)-carbodiimide hydrochloride (Sigma, St. Louis, Mo.) (10 µmoles) in 100 µl of acetonitrile and N-hydroxysuccinimide (4–9 µmoles) in 100 µl of acetonitrile for 12 hours at 25° C. in the dark.

The active ester was mixed with anti-hTSH in PBS buffer containing 0.5% 3-[(3-cholamidopropyl) dimethylammonio]-1-propane-sulfonate ("CHAPS") at pH 6.5 in a ratio of 50:1 (antibody:active ester). After coupling for 3 hours at 25° C., the labeled antibody was dialysed against PBS buffer containing 0.5% CHAPS at pH 6.5 until no free label was present in the dialysate by U.V.

Based on the U.V. spectra, the conjugate had an average of 10 labels per antibody.

B. Assay for hTSH. CLIA and EIA were compared Using the Abbott hTSH-EIA Kit (Abbott Laboratories, Abbott Park, Ill.) with the exception that for the CLIA, the anti-hTSH acridininium conjugate was used in place of the kit anti-hTSH-HRPO conjugate. Thus, a standard curve was generated by incubating the kit standards with the kit beads at 37° C. for 1 hour, then washing three times. For the CLIA, the conjugate prepared above was diluted 1:5000 with PBS buffer containing 50% calf serum, 1% normal mouse serum, 0.05% Tween® 20 and 2 mM EDTA at pH 6.3. One hundred microliters of this solution was incubated with the beads for 1 hour at 37° C., then washed four times.

The beads were transferred one by one to the reaction vial of a luminometer containing 400 µl of water and reacted with 200 µl of 0.03% $H_2O_2$ in 0.2N NaOH. Photon, counts were recorded for 6 seconds.

The EIA was carried out according to the instructions in the kit insert on a Quantum II® spectro photometer (Abbott Laboratories, Abbott Park, Ill.)

The results are shown in Table 9.

TABLE 9

| Concentration (µIu/ml) | CLIA (counts) | EIA ($A_{492}$) |
|---|---|---|
| 0 | 533 (SD35.4) | 0.012 |
| 1 | 5064 | 0.062 |
| 4 | 14476 | 0.176 |
| 10 | 32092 | 0.397 |
| 25 | 66072 | 0.828 |
| 60 | 110,984 | 1.602 |

Under these conditions the sensitivity of the CLIA was 0.016 µIU/ml (0 standard+2 SD) while the EIA had a sensitivity of 0.05 µIU/ml.

EXAMPLE 18

Preparation of 5-methyl-6-[N-tosyl-N-(2-carboxyethyl)]-phenanthridiniumcarboxamide Phenanthridine-6-carboxylic acid (400 mg, 1.8 mmoles) [prepared by the method of Wittig et al., *Justus Liebig's Ann.*, 577, 1 (1952)], was suspended in methylene chloride (20 ml, distilled from $P_2O_5$) and cooled to 0° C. under nitrogen. Oxalyl chloride (320 µl, 3.6 mmoles) (Aldrich Chemical Co., Milwaukee, Wis.) was added, followed by DMF (5 µl). As the reaction mixture was stirred for one hour at 0° C. and for 30 minutes at 25° C., all the carboxylic acid dissolved. The solution was evaporated to dryness to give the acid chloride which was used without further purification.

Methyl N-tosyl-β-alanine was prepared from methyl-β-alanine (Aldrich Chemical Company, Milwaukee, Wis.) and tosyl chloride (Aldrich Chemical Company, Milwaukee, Wis.) according to the procedure of Example 1. Potassium t-butoxide (600 mg, 5.4 mmoles, freshly sublimed) was added to a solution of 1.3 g (5.4 mmoles) of methyl N-tosyl-β-alanine in 50 ml of THF. After stirring for 15 minutes and at room temperature and under $N_2$, the suspension was evaporated to dryness. The potassium salt of methyl N-tosyl-β-alanine, was resuspended in 20 ml of THF, mixed with the acid chloride (in 20 ml of THF), and stirred for 12 hours.

The resulting suspension was poured into 100 ml of ethyl acetate, washed with 50 ml of water and washed twice with 25 ml of brine. After drying over $MgSO_4$ and evaporating to dryness, the residue was chromatographed on a Chromatatron™ chromatograph (available from Harrison Research, Palo Alto, Calif.) using a 4 mm silica rotor and employing a 25/75 ethylacetate/hexane gradient. The product ($R_f$ 0.2) was collected, then recrystallized from benzene/hexane (i.e., the product was dissolved in benzene, and hexane was added until cloudy) to give 130 mg of methyl 6-[N-tosyl-N-(2-carboxyethyl)]-phenanthridinecarboxamide, Compound 84, 13514-225.

Compound 84, 13514-225, was methylated according to the procedure in Example 3 to give methyl 5-methyl-6-[N-tosyl-N-(2-carboxyethyl)]-phenanthridiniumcarboxamide, compound 85, 13514-227. Compound 85 was hydrolyzed according to the procedure in Example 8 to provide 5-methyl-6-[N-tosyl-N-(2-carboxyethyl)]-phenanthridiniumcarboxamide, compound 86, 13514-228.

Compounds 84, 85 and 86 are described using the numerals, symbols and abbreviations as explained in Example 1.

84. 13514-225 Methyl 6-[N-tosyl-N-(2-carboxyethyl)]-phenanthridinecarboxylate. MS M+H @ 463

85. 13514-227 Methyl 5-methyl-6-[N-tosyl-N-(2-carboxyethyl)]-phenanthridiniumcarboxamide. MS $M^+$ @ 477. $M_p$ 136° C.

86. 13514-228 5-Methyl-6-[N-tosyl-N-(2-carboxyethyl)]-phenanthridiniumcarboxamide. MS $M^+$ @ 463

Although the present invention has been described in terms of preferred embodiments, it is understood that modifications and improvements will occur to those skilled in the art.

For example, in light of the results presented herein, it is expected that additional compounds which are useful according to the present invention may be identified by the formula

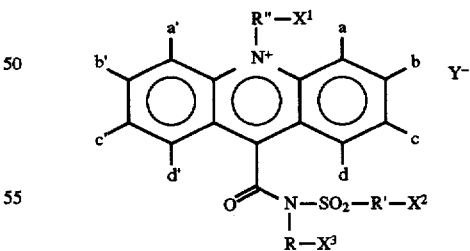

wherein a, b, c, d, $a^1$, $b^1$, $c^1$, $d^1$ independently may be hydrogen, alkyl, aryl, amino, substituted amino, carboxyalkyl, sulfoalkyl, alkoxyl, aryloxy, sulfo, thio alkoxyl, thioaryloxy aminoalkyl, protected aminoalkyl, hydroxyalkyl, protected hydroxyalkyl, haloalkyl, or any adjacent of these positions may be linked so as to form aromatic rings fused to the acridine nucleus.

In addition, Sheehan et al., U.S. Pat. No. 3,539,574 describes chemiluminescent acridinium compounds which are also expected to be useful according to the present invention. Other isomeric acridinecarboxylic acids, quinoline carboxylic acids, isoquinoline carboxylic acid, other activated acridine amides, and other activated acridine esters are expected to be useful according to the present invention. Such compounds include, without limitation: hydroxamates identified by the formula

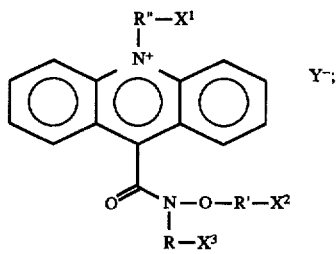

enamides identified by the formula

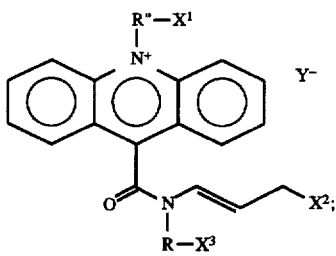

arylamides identified by the formula

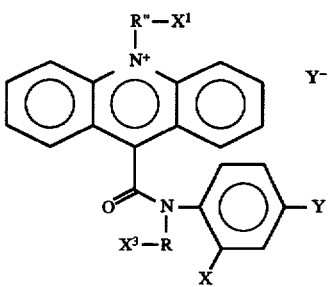

wherein X and Y¹ are electron withdrawing groups; N-heterocycles identified by the formula

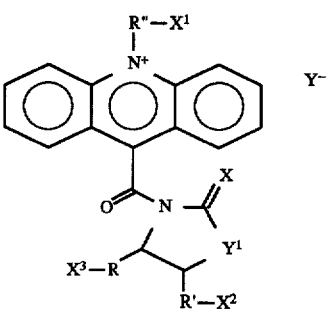

wherein X and Y¹ may independently be O, S, P, N, or C; activated esters such as thiolesters identified by the formula

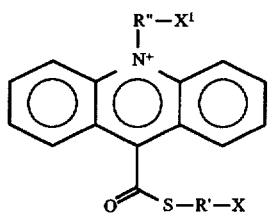

or such as thioesters identified by the formula

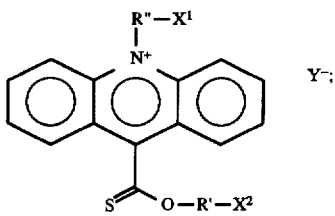

acridine acids identified by the formula

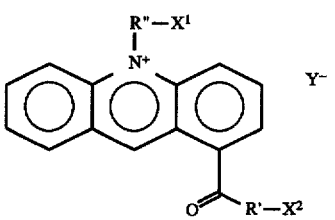

or by the formula

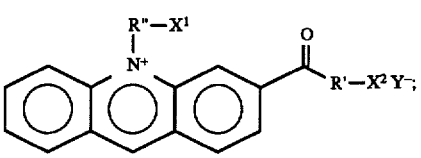

quinoline acids identified by the formula

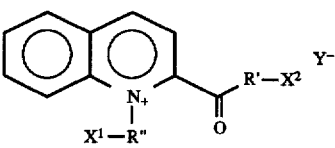

or by the formula

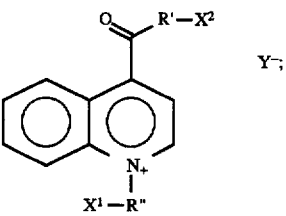

or isoquinoline acids identified by the formula

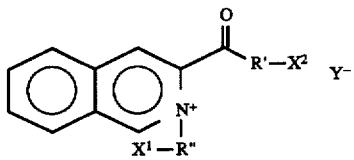

or by the formula

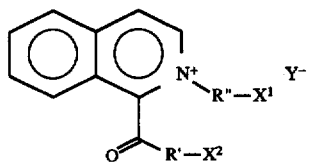

It is understood that those skilled in the art will be enabled by the above specification to incorporate reactive functional groups for attaching the label to an analyte into compounds according to the present invention.

It is also contemplated that compounds according to the present invention will be: used in labeling DNA probes; incorporated into an enzyme substrate wherein the product of the enzymatic reaction is the chemiluminescent compound; and incorporated into systems which involve energy transfer or fluorescent quenching.

Compounds according to the present invention may also be: incorporated into a system which employs the compound as a labeling reagent in a post-column HPLC detection system; used to measure $H_2O_2$ in other analytical systems, including the quantitation of intracellular $H_2O_2$ concentration; and used as a source of intense pulsed light.

Therefore, it is intended that the present invention include all such variations and improvements as come within the scope of the invention as claimed.

What is claimed is:

1. A chemiluminescent conjugate comprising an antibody conjugated to a chemiluminescent compound of the formula:

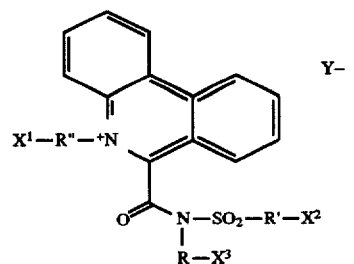

wherein R, R', R", $X^1$, $X^2$ and $X^3$ independently comprise substituents which do not interfere with chemiluminescence measurement, linkage to the antibody is through one of $X^1$, $X^2$ and $X^3$, and wherein $Y^-$ is an anion with the proviso that R—$X^3$ R'—$X^2$ and R"—$X^1$ may be hydrogen, wherein $X^1$, $X^2$ and $X^3$ are independently members of the group consisting of hydrogen, (—$CO_2H$), (—C(=O)$OZ^1$) wherein $Z^1$ is alkyl, (—C(=O)$NZ^2Z^3$) wherein $Z^2$ or $Z^3$ is H, alkyl or aryl, (—C(=O)$OZ^4$) wherein $Z^4$ is aryl, (—CN), (—C(=O)N($Z^5$)—C(=O)—$Z^5$) wherein $Z^5$ is H, alkyl or aryl, (F, Cl, Br, or I), (—N=C=O), (—N=C=S), (—$SO_3^-$), sulfonyl halide (—$SO_2Z^6$) wherein $Z^6$ is (Cl or F), —C(=O) —$Z^7$) wherein $Z^7$ is (F, Cl, or Br),

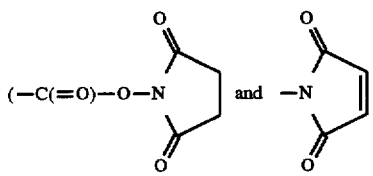

groups;

wherein R independently comprises a member selected from the group consisting of alkylene, alkenylene and substituted alkylene groups and wherein R' and R" independently comprise a member selected from the group consisting of alkylene, arylene, alkenylene, substituted alkylene, and substituted arylene groups, such that:

one or more hydrogens or open valences of said member is replaced by an alkyl, aryl, alkylene, alkenylene, substituted alkyl, substituted alkylene, substituted aryl, alkoxy, aryloxy, halo, nitro, amino, protected amino, substituted amino, hydroxy, protected hydroxy, oxo, thio, imino, mercapto or substituted mercapto group;

or such that one or more carbon atoms of the member is replaced by a heteroatom.

2. In a method for performing a chemiluminescent assay to test for the presence of a member of a specific binding pair which may be present in a test sample wherein said method comprises (a) contacting said test sample suspected of containing said specific binding pair member with a conjugate comprising an antibody attached to a chemiluminescent compound capable of generating a detectable signal, which conjugate specifically reacts with said specific binding pair member and (b) determining the presence of said specific binding pair member by detecting the signal generated by said conjugate, wherein the improvement comprises the step of contacting said test sample suspected of containing said specific binding pair member with said chemiluminescent conjugate as recited in claim 1 wherein said antibody of said conjugate specifically binds said specific binding pair member.

3. A chemiluminescent conjugate comprising an antigen conjugated to a chemiluminescent compound of the formula:

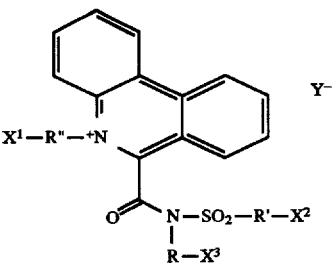

wherein R, R', R", $X^1$, $X^2$ and $X^3$ independently comprise substituents which do not interfere with chemiluminescence measurement, linkage to the antigen is through one of $X^1$, $X^2$ and $X^3$, and wherein $Y^-$ is an anion with the proviso that R—$X^3$ R'—$X^2$ and R"—$X^1$ may be hydrogen, wherein $X^1$, $X^2$ and $X^3$ are independently members of the group consisting of hydrogen, (—$CO_2H$), (—C(=O)$OZ^1$) wherein $Z^1$ is alkyl, (—C(=O)$NZ^2Z^3$) wherein $Z^2$ or $Z^3$ is H, alkyl or aryl, (—C(=O)$OZ^4$) wherein $Z^4$ is aryl, (—CN), (—C(=O)N($Z^5$)—C(=O)—$Z^5$) wherein $Z^5$ is H, alkyl or aryl, (F, Cl, Br, or I), (—N=C=O), (—N=C=S), (—SO$_3^-$), sulfonyl halide (—SO$_2$Z$^6$) wherein Z$^6$ is (Cl or F), (—C(=O)—Z$^7$) wherein Z$^7$ is (F, Cl, or Br),

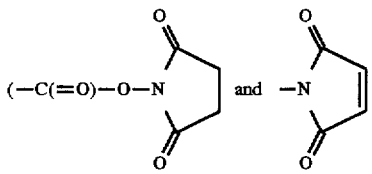

groups;

wherein R independently comprises a member selected from the group consisting of alkylene, alkenylene and substituted alkylene groups and wherein R' and R" independently comprise a member selected from the group consisting of alkylene, arylene, alkenylene, substituted alkylene, and substituted arylene groups, such that:

one or more hydrogens or open valences of said member is replaced by an alkyl, aryl, alkylene, alkenylene, substituted alkyl, substituted alkylene, substituted aryl, alkoxy, aryloxy, halo, nitro, amino, protected amino, substituted amino, hydroxy, protected hydroxy, oxo, thio, imino, mercapto or substituted mercapto group;

or such that one or more carbon atoms of the member is replaced by a heteroatom.

4. In a method for performing a chemiluminescent assay to test for the presence of a member of a specific binding pair which may be present in a test sample wherein said method comprises (a) contacting said test sample suspected of containing said specific binding pair member with a conjugate comprising an antigen attached to a chemiluminescent compound capable of generating a detectable signal, which conjugate specifically reacts with said specific binding pair member and (b) determining the presence of said specific binding pair member by detecting the signal generated by said conjugate, wherein the improvement comprises the step of contacting said test sample suspected of containing said specific binding pair member with said chemiluminescent conjugate as recited in claim 3 wherein said antigen of said conjugate specifically binds said specific binding pair member.

5. A chemiluminescent conjugate formed by a polynucleotide conjugated to a chemiluminescent compound of the formula:

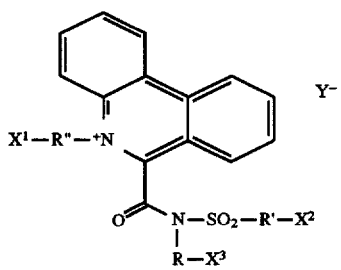

wherein R, R', R", X$^1$, X$^2$ and X$^3$ independently comprise substituents which do not interfere with chemiluminescence measurement, linkage to the polynucleotide is through one of X$^1$, X$^2$ and X$^3$, and wherein Y$^-$ is an anion with the proviso that R—X$^3$ R'—X$^2$ and R"—X$^1$ may be hydrogen, wherein X$^1$, X$^2$ and X$^3$ are independently members of the group consisting of hydrogen, (—CO$_2$H), (—C(=O)OZ$^1$) wherein Z$^1$ is alkyl, (—C(=O)NZ$^2$Z$^3$) wherein Z$^2$ or Z$^3$ is H, alkyl or aryl, (—C(=O)OZ$^4$) wherein Z$^4$ is aryl, (—CN), (—C(=O)N(Z$^5$)—C(=O)—Z$^5$) wherein Z$^5$ is H, alkyl or aryl, (F, Cl, Br, or I), (—N=C=O), (—N=C=S), (—SO$_3^-$), sulfonyl halide (—SO$_2$Z$^6$) wherein Z$^6$ is (Cl or F), (—C(=O)—Z$^7$) wherein Z$^7$ is (F, Cl, or Br),

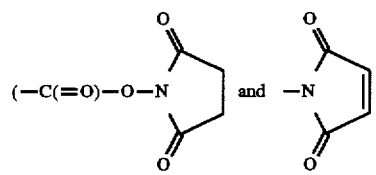

groups;

wherein R independently comprises a member selected from the group consisting of alkylene, alkenylene and substituted alkylene groups and wherein R' and R" independently comprise a member selected from the group consisting of alkylene, arylene, alkenylene, substituted alkylene, and substituted arylene groups, such that:

one or more hydrogens or open valences of said member is replaced by an alkyl, aryl, alkylene, alkenylene, substituted alkyl, substituted alkylene, substituted aryl, alkoxy, aryloxy, halo, nitro, amino, protected amino, substituted amino, hydroxy, protected hydroxy, oxo, thio, imino, mercapto or substituted mercapto group;

or such that one or more carbon atoms of the member is replaced by a heteroatom.

6. In a method for performing a chemiluminescent assay to test for the presence of a polynucleotide which may be present in a test sample wherein said method comprises (a) contacting said test sample suspected of containing said polynucleotide with a conjugate comprising a polynucleotide complementary to said polynucleotide in said test sample which complementary polynucleotide specifically reacts with said polynucleotide of said test sample and which complementary polynucleotide is attached to a chemilumincent compound capable of generating a detectable signal and (b) determining the presence of said polynucleotide by detecting the signal generated by said conjugate, wherein the improvement comprises the step of contacting said test sample suspected of containing said polynucleotide with said chemiluminescent conjugate as recited in claim 5 which polynucleotide of said conjugate is complementary to said polynucleotide in said test sample and wherein said complementary polynucleotide of said conjugate hybridizes with said polynucleotide in said test sample.

7. A chemiluminescent conjugate comprising a non-antibody, binding protein conjugated to a chemiluminescent compound of the formula:

27

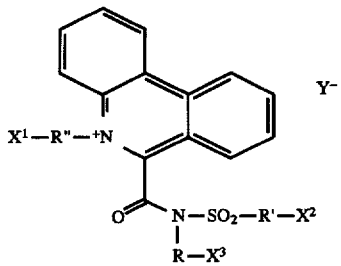

wherein R, R', R", $X^1$, $X^2$ and $X^3$ independently comprise substituents which do not interfere with chemiluminescence measurement, linkage to the non-antibody, binding protein is through one of $X^1$, $X^2$ and $X^3$, and wherein $Y^-$ is an anion with the proviso that R—$X^3$ R'—$X^2$ and R"—$X^1$ may be hydrogen, wherein $X^1$, $X^2$ and $X^3$ are independently members of the group consisting of hydrogen, (—$CO_2H$), (—C(=O) $OZ^1$) wherein $Z^1$ is alkyl, (—C(=O)$NZ^2Z^3$) wherein $Z^2$ or $Z^3$ is H, alkyl or aryl, (—C(=O)$OZ^4$) wherein $Z^4$ is aryl, (—CN), (—C(=O)N($Z^5$)—C(=O)—$Z^5$) wherein $Z^5$ is H, alkyl or aryl, (F, Cl, Br, or I), (—N=C=O), (—N=C=S), (—$SO_3^-$), sulfonyl halide (—$SO_2Z^6$) wherein $Z^6$ is (Cl or F), (—C(=O) —$Z^7$) wherein $Z^7$ is (F, Cl, or Br),

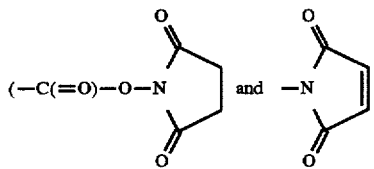

groups;

wherein R independently comprises a member selected from the group consisting of alkylene, alkenylene and substituted alkylene groups and wherein R' and R" independently comprise a member selected from the group consisting of alkylene, arylene, alkenylene, substituted alkylene, and substituted arylene groups, such that:

one or more hydrogens or open valences of said member is replaced by an alkyl, aryl, alkylene, alkenylene, substituted alkyl, substituted alkylene, substituted aryl, alkoxy, aryloxy, halo, nitro, amino, protected amino, substituted amino, hydroxy, protected hydroxy, oxo, thio, imino, mercapto or substituted mercapto group;

or such that one or more carbon atoms of the member is replaced by a heteroatom.

8. In a method for performing a chemiluminescent assay to test for the presence of a complementary analyte of a non-antibody, binding-protein which may be present in a test sample wherein said method comprises (a) contacting said test sample suspected of containing said complementary analyte of said non-antibody, binding protein with a conjugate comprising a non-antibody, binding protein which specifically reacts with said complementary analyte of said non-antibody, binding protein and which non-antibody, binding-protein is attached to a chemiluminescent compound capable of generating a detectable signal and (b) determining the presence of said complementary analyte of said non-antibody, binding protein by detecting the signal generated by said conjugate, wherein the improvement com-

28 prises the step of contacting said test sample suspected of containing said complementary analyte with said chemiluminescent conjugate as recited in claim 7 wherein said non-antibody, binding-protein of said conjugate specifically binds said complementary analyte.

9. A chemiluminescent conjugate comprising a hapten conjugated to a chemiluminescent compound of the formula:

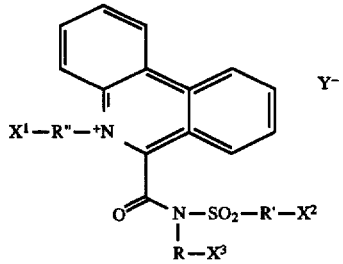

wherein R, R', R", $X^1$, $X^2$ and $X^3$ independently comprise substituents which do not interfere with chemiluminescence measurement, linkage to the hapten is through one of $X^1$, $X^2$ and $X^3$, and wherein $Y^-$ is an anion with the proviso that R—$X^3$ R'—$X^2$ and R"—$X^1$ may be hydrogen, wherein $X^1$, $X^2$ and $X^3$ are independently members of the group consisting of hydrogen, (—$CO_2H$), (—C(=O) $OZ^1$) wherein $Z^1$ is alkyl, (—C(=O)$NZ^2Z^3$) wherein $Z^2$ or $Z^3$ is H, alkyl or aryl, (—C(=O)$OZ^4$) wherein $Z^4$ is aryl, (—CN), (—C(=O)N($Z^5$)—C(=O)—$Z^5$) wherein $Z^5$ is H, alkyl or aryl, (F, Cl, Br, or I), (—N=C=O), (—N=C=S), (—$SO_3^-$), sulfonyl halide (—$SO_2Z^6$) wherein $Z^6$ is (Cl or F), (—C(=O) —$Z^7$) wherein $Z^7$ is (F, Cl, or Br),

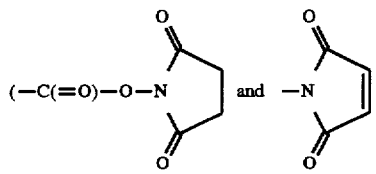

groups;

wherein R independently comprises a member selected from the group consisting of alkylene, alkenylene and substituted alkylene groups and wherein R' and R" independently comprise a member selected from the group consisting of alkylene, arylene, alkenylene, substituted alkylene, and substituted arylene groups, such that: p2 one or more hydrogens or open valences of said member is replaced by an alkyl, aryl, alkylene, alkenylene, substituted alkyl, substituted alkylene, substituted aryl, alkoxy, aryloxy, halo, nitro, amino, protected amino, substituted amino, hydroxy, protected hydroxy, oxo, thio, imino, mercapto or substituted mercapto group;

or such that one or more carbon atoms of the member is replaced by a heteroatom.

10. In a method for performing a competitive chemiluminescent assay to test for the presence of a hapten which may be present in a test sample wherein said method comprises (a) contacting said test sample suspected of containing said hapten with a known amount of an anti-hapten antibody specific for said hapten and with a conjugate comprising a hapten which competes with said hapten in said test sample for binding with said anti-hapten antibody and wherein said hapten of said conjugate is attached to a chemiluminescent compound capable of generating a detectable signal and (b) determining the presence of said hapten in said test sample by detecting the signal generated by said conjugate, wherein the improvement comprises the step of contacting said test sample suspected of containing said hapten with said chemiluminescent conjugate as recited in claim 9 wherein said hapten of said conjugate competes with said hapten in said test sample for specific binding to said anti-hapten antibody.

11. A chemiluminescent conjugate comprising a small molecular weight analyte which binds to a binding protein conjugated to a chemiluminescent compound of the formula:

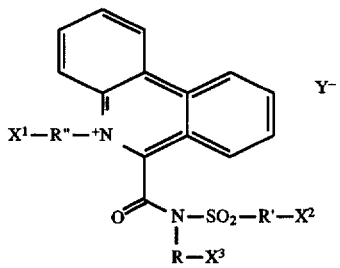

wherein R, R', R", $X^1$, $X^2$ and $X^3$ independently comprise substituents which do not interfere with chemiluminescence measurement, linkage to the small molecular weight analyte is through one of $X^1$, $X^2$ and $X^3$, and wherein $Y^-$ is an anion with the proviso that R—$X^3$ R'—$X^2$ and R"—$X^1$ may be hydrogen, wherein $X^1$, $X^2$ and $X^3$ are independently members of the group consisting of hydrogen, (—$CO_2H$), (—C(=O)O$Z^1$) wherein $Z^1$ is alkyl, (—C(=O)N$Z^2Z^3$) wherein $Z^2$ or $Z^3$ is H, alkyl or aryl, (—C(=O)O$Z^4$) wherein $Z^4$ is aryl, (—CN), (—C(=O)N($Z^5$)—C(=O)—$Z^5$) wherein $Z^5$ is H, alkyl or aryl, (F, Cl, Br, or I), (—N=C=O), (—N=C=S), (—$SO_3^-$), sulfonyl halide (—$SO_2Z^6$) wherein $Z^6$ is (Cl or F), (—C(=O)—$Z^7$) wherein $Z^7$ is (F, Cl, or Br),

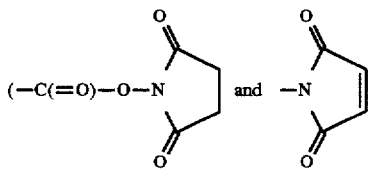

groups;

wherein R independently comprises a member selected from the group consisting of alkylene, alkenylene and substituted alkylene groups and wherein R' and R" independently comprise a member selected from the group consisting of alkylene, arylene, alkenylene, substituted alkylene, and substituted arylene groups, such that:

one or more hydrogens or open valences of said member is replaced by an alkyl, aryl, alkylene, alkenylene, substituted alkyl, substituted alkylene, substituted aryl, alkoxy, aryloxy, halo, nitro, amino, protected amino, substituted amino, hydroxy, protected hydroxy, oxo, thio, imino, mercapto or substituted mercapto group;

or such that one or more carbon atoms of the member is replaced by a heteroatom.

12. In a method for performing a competitive chemiluminescent assay to test for the presence of a small molecular weight analyte which binds to a binding protein and which may be present in a test sample wherein said method comprises (a) contacting said test sample suspected of containing said small molecular weight analyte with a known amount of said binding protein specific for said small molecular weight analyte and with a conjugate comprising a small molecular weight analyte which competes with said small molecular weight analyte in said test sample and which binds to said binding protein, wherein said small molecular weight analyte of said conjugate is attached to a chemiluminescent compound capable of generating a detectable signal and (b) determining the presence of said small molecular weight analyte by detecting the signal generated by said conjugate, wherein the improvement comprises the step of contacting said test sample suspected of containing said small molecular weight analyte with said chemiluminescent conjugate as recited in claim 11 wherein said small molecular weight analyte of said conjugate competes with said small molecular weight analyte in said test sample for specific binding to said binding protein.

13. The chemiluminescent conjugate of any one of claims 1, 3, 5, 7, 9 or 11 wherein said heteroatam is selected from the group consisting of nitrogen, phosphorus, sulfur and oxygen.

14. The chemiluminescent conjugate of any one of claims 1, 3, 5, 7, 9 or 11 wherein R independently is of the formula —$(CH_2)_n$—, wherein n=0–50.

* * * * *